United States Patent [19]

Casanova et al.

[11] Patent Number: 5,364,964
[45] Date of Patent: Nov. 15, 1994

[54] PROCESS FOR PREPARING 1,2,3,4-BUTANETETRACARBOXYLIC ACID

[75] Inventors: Eduardo A. Casanova, Ballwin; Dennis J. Kalota, Fenton, both of Mo.

[73] Assignee: Monsanto Company, St. Louis, Mo.

[21] Appl. No.: 143,596

[22] Filed: Nov. 1, 1993

Related U.S. Application Data

[62] Division of Ser. No. 450,760, Dec. 14, 1989, Pat. No. 5,298,653.

[51] Int. Cl.$^5$ ............................................. C07C 55/24
[52] U.S. Cl. .................................................... 562/590
[58] Field of Search ......................................... 562/590

[56] References Cited

U.S. PATENT DOCUMENTS 5,248,396 9/1993 Casanova et al. ................. 204/59 R

*Primary Examiner*—José G. Dees
*Assistant Examiner*—Joseph Conrad
*Attorney, Agent, or Firm*—W. W. Brooks

[57] ABSTRACT

Butanetetracarboxylic acid with acceptably low levels of color-causing contaminants, suitable for permanent press agent use, is prepared in high conversion and yield from tetraalkyl butanetetracarboxylates by a series of steps including purification of precursor material, hydrolysis with high concentration of acid catalyst, and oxidative purification of product.

5 Claims, 4 Drawing Sheets

PROCESS FOR PREPARING 1,2,3,4-BUTANETETRACARBOXYLIC ACID

This is a division of application Ser. No. 07/450,760, filed Dec. 14, 1989 now U.S. Pat. No. 5,298,653.

BACKGROUND OF THE INVENTION

1. Field of the Invention

The present invention concerns a process for preparing 1,2,3,4-butanetetracarboxylic acid with acceptably low levels of color-forming materials, by steps involving purification of a tetraalkyl butanetetracarboxylate precursor material and hydrolysis of the precursor, and oxidative treatment for purification of the resulting butanetetracarboxylic acid.

The compound 1,2,3,4-butanetetracarboxylic acid has been found by the U.S. Department of Agriculture to be an effective permanent press agent for polyester-cotton blend fabrics, and the compound could find use in large quantities for such purpose. Accordingly, an efficient process for preparing the compound could be very useful. Such a process must produce a product of acceptable color performance properties, as this is an important factor for suitability for permanent press agents. The tetraalkyl butanetetracarboxylates used as reactants in the present process can be prepared from dialkyl maleates by an electrolytic hydrodimerization process as described and claimed in commonly assigned copending application Ser. No. 07/450,773.

2. Description of the Related Art

Procedures have been reported in which 1,2,3,4-butanetetracarboxylic acid is prepared by oxidative cleavage of tetraphthalic acid or anhydride by oxidation with ozone-containing gas, followed by oxygen-containing gas, with the mixture then being heated with a peroxide, e.g. $H_2O_2$, at 100° C. to produce the butanetetracarboxylic acid See Japanese patent 55/49336 [80/493363], Apr. 9, 1980, *Chem. Abstracts* 93 (13) 132082h; and Japanese patent 54/151906 [79/151906], Nov. 29, 1979, *Chem. Abstracts* 92 (23) 197937 g. Also reported is a procedure in which Delta-4-tetrahydrophthalic anhydride was oxidized with $HNO_3$, then stirred one hour at 90° C. (oxidative post treatment) to give 1,2,3,4-butanetetracarboxylic acid free of $HNO_3$, which gave no color on heating 30 minutes at 140° C. in ethylene glycol. Polycarboxylic acids from the $HNO_3$ oxidation of $C_{3-33}$ cycloalkenes were purified by an oxidative post treatment; see German Offen. DE 3016225 A1, Oct. 29, 1981, *Chem. Abstracts* 96 (3) 19672z.

It is known that various organic esters can be converted to free acids by hydrolysis procedures, employing acid, base, or other catalysts, although desirable hydrolysis procedures and conditions may vary considerably with the esters involved. It is also known that in equilibrium reactions, in accord with the law of mass action, the forward reaction rate is generally a function of the concentration of reactants, while the reverse reaction rate is generally a function of the concentration of products. Procedures which give high yields and good production rates are advantageous for commercial production.

SUMMARY OF THE INVENTION

The present invention concerns a process for preparing 1,2,3,4-butanetetracarboxylic acid (BTCA) of high purity and very low or negligible levels of color-causing materials, from tetraalkyl butanetetracarboxylates (TABTC) utilizing efficient reactions, conditions and procedures which give good yields and recoveries of product having good purity and acceptable performance in color tests. In a particular aspect the invention involves hydrolyzing a tetracarboxylate to the butanetetracarboxylic acid utilizing relatively high TABTC and acid contents, compared to water, so as to give a good reaction rate and desirably short reaction time, such as within six hours; and distilling over alkanol and water during the hydrolysis to drive the reaction to completion while adding additional water to replace that distilled.

The invention also involves crystallizing the tetraalkyl butanetetracarboxylate from alkanol before the hydrolysis step in order to separate certain byproducts from the tetracarboxylate, and particularly in the case of tetramethyl butanetetracarboxylate (TMBTC), crystallizing from methanol at sub-zero (celsius) temperatures, e.g. near −10° C., and also optionally adding water to aid in the separation and high recovery.

The invention further involves subjecting the butanetetracarboxylic acid to oxidation with an oxidizing agent to effect oxidation of color-causing materials, with an oxidation with aqueous hydrogen peroxide at elevated temperatures up to 55° C. followed by higher temperatures to destroy excess peroxide, being very effective.

The invention can also advantageously use, prior to the hydrolysis step, an aqueous washing procedure in which the tetraalkyl butanetetracarboxylate, at temperature above its melting point, is extracted with an aqueous liquid, e.g. water, in order to remove salts and other water soluble impurities, including some color-causing materials. The invention can also employ a crystallization procedure as a convenient and efficient means to separate the butanetetracarboxylic acid product from aqueous solution, with cooling to ambient temperatures generally being sufficient to effect crystallization. The fraction of butanetetracarboxylic acid which does not separate can be recycled with filtrate, containing residual acid catalyst, to the hydrolysis step.

The present invention provides a process for preparing butanetetracarboxylic acid from tetraalkyl butanetetracarboxylates with high yield and recovery, e.g. about 83%, by a series of relatively simple reactions and operations which can be accomplished with industrially practical equipment and with reasonable production rates.

The invention can also employ a step in which residual acid catalyst in the BTCA product material is partially or completely neutralized by base, e.g. NaOH.

DESCRIPTION OF THE PREFERRED EMBODIMENTS

Figure 1:
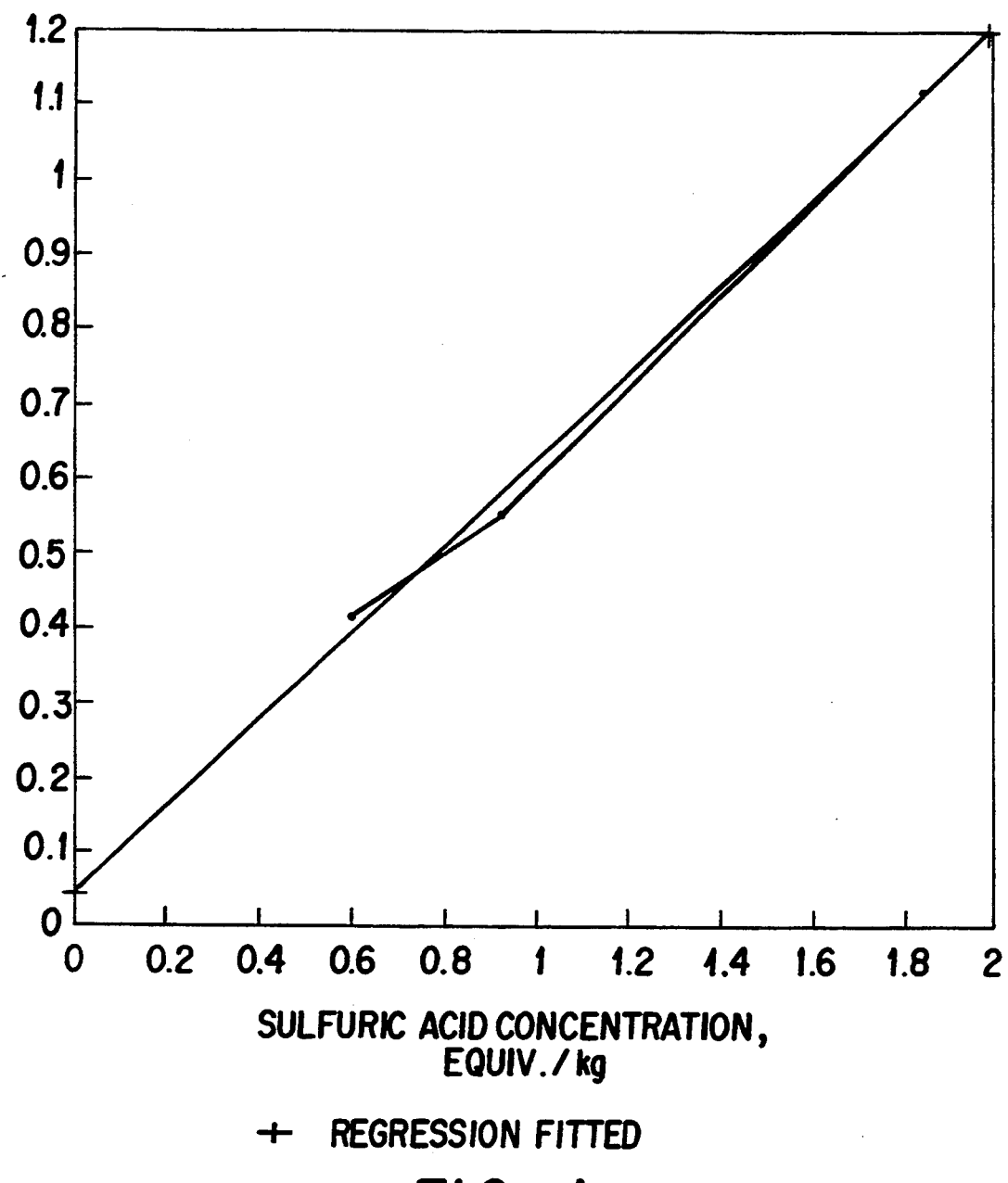
FIG. 1 is a graph of TMBTC hydrolysis rate constant vs. acid concentration.

The present process for converting tetraalkyl butanetetracarboxylates to butanetetracarboxylic acid involves a hydrolysis to form the acid, and also various isolation and purification procedures in order to obtain product of acceptable purity and lack of objectionable levels of color-causing contaminants.

The exemplary process includes the following steps:
1. Filtration of TMBTC methanol solution to remove particulates;
2. Crystallization of TMBTC from solution and separation by filtration or contrifugation;
3. Extraction of TMBTC with water to remove salts and water soluble organic compound;
4. Hydrolysis of TMBTC to produce BTCA;
5. Oxidation of BTCA solution to remove color-forming impurities;
6. Crystallization of the BTCA from aqueous solution and separation by filtration or centrifugation; and
7. Washing the crystalline BTCA with water to remove residual acid; or
7A. Removing residual acid by partial or complete neutralization with base, such as sodium hydroxide, and separating the crystalline BTCA by filteration or centrifugation.

At times there may be a preference to provide the BTCA in aqueous solution for use, rather than separating and washing it as in steps 6 and 7 above. While removal of residual acid is important for comparison purposes as the acid has a significant effect upon color development, in some applications the effect of the acid can be countered by and left to subsequent treatments.

In the exemplary process, tetramethyl butanetetracarboxylate is used as exemplary of tetraalkyl butanetetracarboxylates, which can be employed in the process under similar conditions, generally employing the corresponding alkanol as solvent. Since TMBTC serves very well as an intermediate to prepare the desired BTCA there will ordinarily be no need to use other tetraalkyl butanetetracarboxylate esters to prepare BTCA. However, tetraethyl butanetetracarboxylate and ethyl alcohol can be used under similar conditions with similar results.

The hydrolysis reaction involved in the present invention is represented:

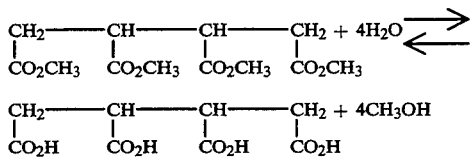

The reaction involves reaction of water with the tetramethyl ester, and in such reactions the amount of reaction, or equilibrium concentrations of the reaction, depends upon the concentration of the reactants, including the water. The reaction can be driven to the right, improving the conversion of the tetramethyl butanetetracarboxylate, by increasing the water concentration. Often hydrolysis reactions employ a very large amount of water, with the ester to be hydrolyzed constituting, for example, only about 10% by weight of the hydrolysis solution. Also such reactions are typically effected with fairly dilute acid concentrations, e.g. about 1 to 5% acid by weight. With tetramethyl butanetetracarboxylate, it has been found that low ester and low acid concentrations give very poor reaction rates. Such low rates would necessitate batch reaction time of 20 to 24 hours or so. In the present invention it has been found that high concentrations of TMBTC and acid give good reaction rates and permit relatively short batch reaction times, such as 4 to 5 hours or so. In such reactions, the TCA is present in weight concentrations upwards to 20%, such as in a range of about 25 to 35% or more of the hydrolysis reaction mixture. The acid, such as sulfuric acid, is employed in amounts constituting more than 5% by weight of the reaction mixture and more than 10% by weight of the water present in the hydrolysis mixture. Considering the total hydrolysis mixture, it is advantageous to have at least one gram-equivalent acid per kg of hydrolysis mixture. In order to have good acid strength, it is advantageous to limit the amount of water present. However, water is a reactant for the hydrolysis and is needed for this purpose.

In an exemplary procedure herein, a desired limited amount of water is added initially, and as water is used in the reaction, or removed by distillation, additional amounts of water are added to maintain approximately the original water content. During the hydrolysis, methanol is removed by distillation in order to drive the reaction to completion by removing a product; and water is distilled along with the methanol. It happens that a relatively large amount of water is employed during the course of the hydrolysis with, for example, a total of 1454 parts water being added and 1438 parts being removed by distillation in an operation in which about 260 parts water was present initially. The present invention includes a procedure in which water content in the hydrolysis mixture is relatively limited, such as near 50% or so or in the range of about 50% to about 75%, and large additional amounts of water are added to replace water as it is removed during the hydrolysis, such as more than 3 or 4 times the initial water provided. The controlled water content is used in conjunction with relatively high acid concentrations, such as more than 10% by weight of the water present. In regard to the total reaction mixture, it is desirable to have at least 0.6 gram equivalent acid per kg of reaction mixture, and advantageously, more than about one gram equivalent acid, and more than 1.5 gram-equivalents acid has further advantage.

Several hydrolysis procedures involving hydrolysis of tetramethylbutanetetracarboxylate were carried out as described in Examples 1 through 6 below, and the procedures are summarized in Table 1. Data from Examples 3 through 6 have also been used for graphs illustrating the effects of temperature and concenration upon hydrolysis rate, as presented in FIGS. 1 through 3, and further described below.

Hydrolysis of Tetraalkyl Butanetetracarboxylates

EXAMPLE 1

To a 1-liter flask was added 43.8 g (0.151 mole) of tetramethyl 1,2,3,4-butanetetracarboxylate, 589.3 g of deionized water, and 0.79 g (6.8 mole) of phosphoric acid. The flask was fitted with a mechanical stirrer and a distillation head. The flask was heated and a mixture of water and methanol distilled overhead. The conversion was followed by analyzing for the amount of methanol collected. An additional 408.9 g water was added at 2.75 hour. An additional 2.37 g of 85% phosphoric acid was added at 4.2 hour. At 7 hours 389.7 g of water was added. The reaction mass was again heated at reflux overnight. Distillation was later continued. At 50.3 hours an additional 254.8 g of water was added. Distillation was stopped at 54 hours. At this time the cumulative methanol analyses indicated a 90% conversion of the esters to the free carboxylic acids. The reaction mass temperature through all but the first 20 minutes was 100° C.

The procedure described above was fragmented, over several work days, due to the long reaction time caused by the low reactivity of the tetramethyl 1,2,3,4-butanetetracarboxylate. Essentially, the reactor charge consisted of 6.9 wt % tetramethyl 1,2,3,4-butanetetracarboxylate, 0.5% phosphoric acid, and 92.6% water. Methanol was continuously distilled from the reactor as a methanol and water distillate. Water was added to replace the distillate. The reaction temperature was 100° C. Under these conditions the conversion of ester to free acid was 90% complete in 54 hours. This procedure is summarized in Table 1 as reaction #1.

EXAMPLE 2

Benzenesulfonic acid was used as the hydrolysis catalyst. To a 1-liter four neck flask was added 28.5 g of TMBTC, 502.2 g of deionized water and 6.6 g of benzenesulfonic acid consisting of a 1.1 g initial charge, a 2.2 g addition after 1.1 hours, and a 3.3 g after 2.5 hours. The methanol was stripped as it formed. Water was added at 1.05 hours and 2.25 hours into the run at amounts of 423.6 g and 403.0 g respectively. Three distillation cuts were collected. These were a 316.6 g cut at one hour, a 450.9 g cut at 2.2 hours, and a 520.6 g cut at 3.6 hours. At this point the reaction was discontinued. Analysis of the distillatas found that the reaction was 60% completed after 3.6 hours.

EXAMPLE 3

Sulfuric acid was used as a hydrolysis catalyst. To a 500 ml four-neck flask fitted with a distillation head and condenser, and an addition funnel was added 68.4 g (0,235 mol) of tetramethyl 1,2,3,4-butanetetracarboxylate and a 129.5 g of water. This mixture was heated to 100° C. Then 20.6 g of concentrated sulfuric acid (95.5%, 0.201 mol) was added. Throughout most of the run the pot temperature was 103° C. The methanol formed by the reaction and some water was continuously stripped from the reactor. Water was continuously added to maintain a constant mass in the reactor. The reaction was 99.8% completed after 5 hours.

EXAMPLE 4

The hydrolysis reaction of Example 3 was repeated but with less sulfuric acid catalyst. The reactor charges were 68.7 g (0.236 mol) of the tetraester and 142.8 g of water. This mixture was heated to 100° C. Then 6.73 g of concentrated sulfuric acid (95.5%, 0.065 mol) was added. The procedure was carried out in the same way as the above example that used 20.6 g of acid. A 97.0% conversion was obtained in 8.5 hours at 101° C. The example using 20.6 g achieved a 97% conversion in 3.1 hours. In the present example, conversion was only about 94% at 6.5 hours.

EXAMPLE 5

The conditions of Example 3 were repeated except that the temperature of the reaction mass was maintained at 80° C. by controlling the pressure 54.0 kPa at (405 torr) to 58.7 kPa (440 torr). The equipment described in the preceding examples was charged with 68.4 g (0,236 mol) of tetramethyl 1,2,3,4-butanetetracarboxylate, and 129.4 g of water. The mass was heated to 78° C. Then 20.4 g of concentrated sulfuric acid (95.5%, 0.199 mol) was added. The reactor pressure was adjusted to maintain an 80° C. reaction temperature. This reaction was 94% completed in 9.4 hours. The same experiment but at a 103° C. reaction temperature, achieved a 94% conversion in 2.7 hours.

EXAMPLE 6

Hydrolysis was conducted in accord with the procedure of Example 1, but utilizing 10.3 g (0,100 mol) of 95.5% sulfuric acid. A reaction time of 5 hours gave a 94.7% conversion.

TABLE 1

| Expl. # | TMBTC Grams | TMBTC Moles | $H_2SO_4$ Grams | Initial Water Grams | Added Water Grams | Reac Time Hours | Reac Temp. °C. | Conv. % |
|---|---|---|---|---|---|---|---|---|
| 1 | 43.8 | 0.151 | 3.2* | 589.3 | 1740.7 | 54.0 | 100 | 90.5 |
| 2 | 28.5 | 0.0982 | 6.6** | 502.2 | 826.6 | 3.6 | 102 | 60.0 |
| 3 | 68.4 | 0.235 | 20.6 | 129.5 | 685.1 | 5.0 | 103 | 99.8 |
| 4 | 68.7 | 0.236 | 6.73 | 142.8 | 1485.8 | 8.5 | 101 | 97.0 |
| 5 | 68.4 | 0.236 | 20.4 | 129.4 | 1669.7 | 9.4 | 80 | 93.8 |
| 6 | 68.5 | 0.236 | 10.3 | 139.3 | 623.1 | 5.0 | 102 | 94.7 |

*Phophoric acid as catalyst.
**Benzenesulfonic acid as catalyst.

In Examples 1 and 2 of the Table, large amounts of water and low acid concentrations were used, as often employed in typical hydrolysis reactions, and very slow reactions resulted. In Example 3 a lower amount of water and high concentration of acid was used, providing about 1.83 gram equivalents acid per kg of reaction mixture, and a much faster reaction was obtained. In Example 4 the acid concentration was still fairly strong, but much lower than that in Example 3 with a corresponding drop in reaction rate. From the reaction rates of Examples 3, 4, and 6, rate constants for the reaction were plotted against sulfuric acid concentration, as illustrated in FIG. 1. It can be seen that the rate increases in essentially a straight-line relationship with increase in acid concentration. The results fit (by regression fit) the relationship:

$$K = 0.580638 \text{ (gram-equiv. } H_2SO_4/kg) + 0.045685$$

There is advantage in using a high enough acid concentration to get a good reaction rate, such as at least 1 gram-equivalent $H_2SO_4$ per kg of reaction mixture, and a rate constant of at least 0.6 hour $-1$, and reaction rates sufficient to complete a batch reaction within about 6 hours. It will be preferred to utilize acid concentrations of more than 1.5 gram equivalents acid per kg reaction mixture.

Figure 2:
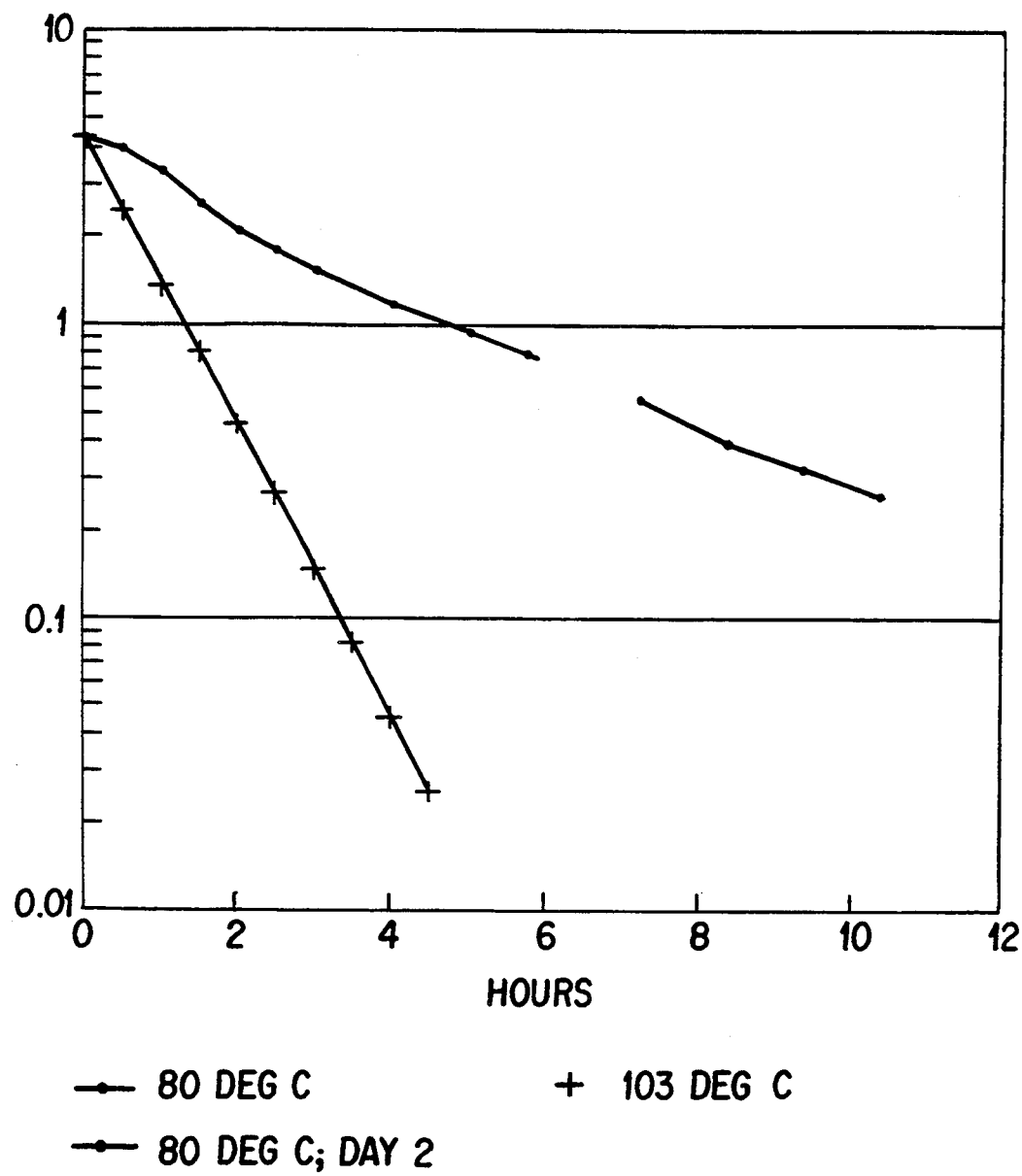
FIG. 2 is a graph showing TMBTC hydrolysis vs. time at different temperatures.

In FIG. 2 hydrolysis reactions at two different temperatures (Examples 3 and 5 above) are plotted in terms of equivalents of unhydrolyzed ester per kg of reaction mixture vs. reaction time. The results on semi-log paper show a consistent decline in both cases, with the reaction at 103° C. (Example 3) being essentially complete in slightly more than four hours, while that at 80° C. (Example 5) was far from complete after 10 hours, with a trend indicating a much longer time would be needed for completion. These results indicate it is very important to use a relatively high reaction temperature, such as upwards of 95° C., or near or over 100° C., in order to have a good reaction rate. Hydrolysis under pressure at temperatures over 100° C. would be desirable.

Figure 3:
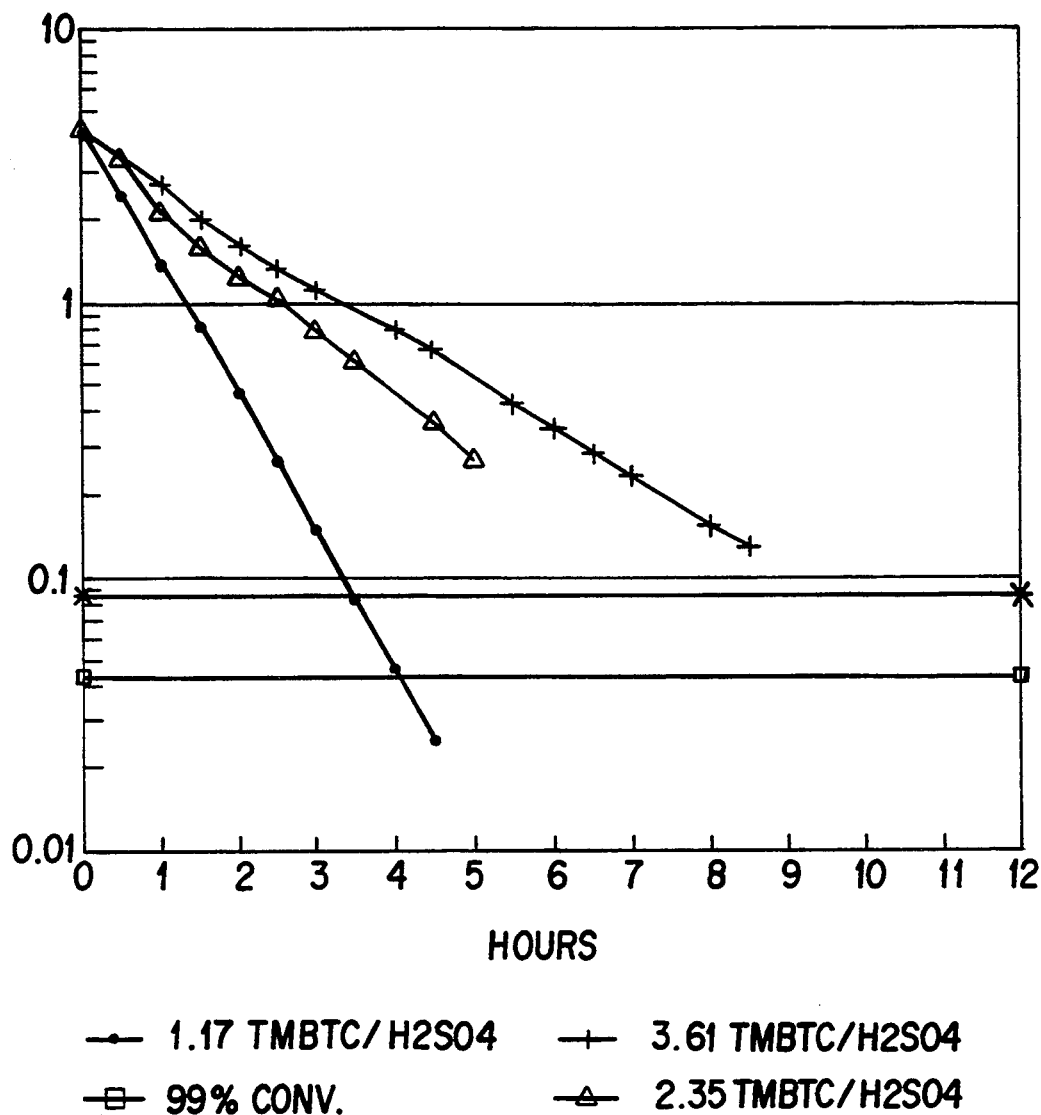
FIG. 3 is a graph showing TMBTC hydrolysis vs. time for different $TMBTC/H_2SO_4$ mole ratios.

In FIG. 3, hydrolysis results of Examples 3, 4, and 6 are plotted on semi-log paper for reactions employing different mole ratios of TMBTC to $H_2SO_4$, the ratios being 1.17 (Example 3), 3.61 (Example 4) and 2.3 (Example 6). The reaction with the 1.17 $TMBTC/H_2SO_4$ ratio was essentially complete within 5 hours, while the other reactions were slower with the trend of the 3.61 $TMBTC/H_2SO_4$ reaction indicating over 9 hours to reach the 97% conversion line (the line marked by asterisks below the 0.1 line). These results indicate the advantage in using relatively low $TMBTC/H_2SO_4$ mole ratios, such as not over about 2.

Good reaction rates and short reaction times have the advantage of permitting good production rates with the equipment employed. An additional consideration is that batch runs of less than 8 hours, such as less than 6 hours, are very advantageous for fitting into normal work schedules. The hydrolysis reaction mixture with TMBTC as reactant involves water and methanol, so 103° C. is about the highest temperature obtainable during most of the reaction, although temperatures up to 111° C. or so are obtained as methanol and some water are removed in the later part of the reaction. Higher temperatures could be obtained by employing pressure or possibly by regulating the components. The amount of methanol in the reaction mixture affects the reaction temperature, possibly keeping it at 100° C. or so if methanol is permitted to build up before being removed by distillation. Accordingly, it is advantageous to provide heating sufficient to distill methanol from the reaction mixture at a good rate. The presence of methanol also tends to retard the reaction, since it is a product in an equilibrium reaction, and this is an additional reason for removing it. In the distillation water is also removed at a relatively high rate and replaced by additional water to provide water for the reaction. The total water supplied in the hydrolysis procedure is generally at least four times the amount present on the average during the hydrolysis procedure.

A sample of BTCA will ordinarily contain some color-causing materials. These materials may be color bodies which actually give the BCTA a color, ordinarily yellow; or materials which form color when the BCTA is heated. For test purposes, color was developed in samples by heating in a vacuum oven for at least 24 hours. Color-causing materials can be neutralized or removed to a great extent by a peroxide treatment. The treatment procedure involves adding a small amount of hydrogen peroxide to the BCTA hydrolysate solution and agitating at moderately elevated temperature, e.g. 55° C. for a short time, sufficient for reaction, such as 30 minutes or more. The mixture is then heated to reflux, ordinarily about 106° C., to decompose excess peroxide and peracids. It is contemplated that this can be accomplished in about 30 minutes, but may take much longer, a number of hours, in the absence of metal contaminants or other materials to catalyze the decomposition.

EXAMPLE 7

In this Example, a peroxide treatment, following a hydrolysis of TMBTC, is described.

To a 500 ml four-neck flask was added 86.2 g (0.297 mol) of TMBTC and a mixture of 26.0 g (0.265 mol) of concentrated (95.5%) sulfuric acid in 163.3 g of water. This mixture was mechanically stirred and heated to effect a hydrolysis of the tetraester. A mixture of methanol and water was continuously distilled from the flask. Water was added to the flask to maintain a constant mass. After 7.5 hours the hydrolysis was completed. There was recovered 161.6 g of a light yellow hydrolysate solution containing the BTCA. A 100.0 g aliquot of the hydrolysate solution was returned to the 500 ml flask. To the hydrolysate was added 1.02 g of 30% hydrogen peroxide ($H_2O_2$). The solution was slowly heated to a reflux temperature of 110° C. The solution was frequently tested for the presence of peroxides with starch-iodide paper. The solution gave a negative test after 9.75 hours of refluxing. The heating to reflux in the procedure was slow enough to allow considerable time for reaction in the 50° to 60° C. range.

Characterization of Butanetetracarboxylic Acid

EXAMPLE 8

A number of different samples of BCTA were appraised for color in accord with the following test. The parameters and results are reported in Table 2.

The color level of BTCA samples was appraised by spectrophotometry. Some samples were heated as solids to 89° C. prior to testing. Color determinations were made on 10% solutions of samples in either aqueous KOH, or deionized water. The UV/visible spectrum (200 nm to 800 nm) was obtained for each sample using an HP8451A diode-array spectrophotometer. An absorbence measurement was recorded at a single wavelength, 400 nm, in the visible region. While color is the sum of many wavelengths, the absorbance at 400 nm provides a secondary measurement of the color of each solution. Also, BCTA alone does not absorb light at 400 nm.

TABLE 2

| ABSORBANCE AT 400 nm of BTCA WATER SOLUTIONS | | | | |
|---|---|---|---|---|
| Sample Description | $H_2O_2$ Treated | Heated at 89° C. | 400 nm Absorb | Factor |
| Laboratory BTCA | Yes | No | 0.01094 | 1.0 |
| Pilot Plant BTCA after neutralization of $H_2SO_4$ | Yes | Yes | 0.016891 | 1.5 |
| Pilot Plant BTCA Containing residual $H_2SO_4$ | No | Yes | 1.42019 | 129.8 |
| Pilot Plant BTCA recrystallized from water | No | Yes | 0.886947 | 81 |
| Pilot Plant BTCA containing residual $H_2SO_4$ | Yes | Yes | 0.181747 | 16.6 |
| Laboratory Prepared BTCA | No | No | 0.02745 | 2.5 |
| Laboratory BTCA TMBTC not water extracted | Yes | Yes | 0.01533 | 1.4 |
| Laboratory BTCA TMBTC extracted once with water | Yes | Yes | 2.021621 | 184.8 |
| Commercial BTCA #1 | No | No | 0.021621 | 2.0 |
| Commercial BTCA #1 | No | Yes | 0.043579 | 4.0 |

In Table 2 BTCA from this process was used to provide a base line and assigned a Factor of 1. The other factors are calculated from the ratio of a sample's absorbance, compared to the base line BTCA. The results with pilot plant BTCA show that marked improvement can be obtained by recrystallization, or peroxide treatment, or neutralization of residual sulfuric acid a. The results with laboratory prepared BTCA marked improvement is obtained by peroxide treatment. The benefit of the water extraction of TEMBTC is also demonstrated. The results also indicate that color purity can be obtained better than that of a commercial sample, with the sample after neutralization of sulfuric acid having only 40% the absorbance of a commercial sample subjected to the same heat treatment. The commercial sample #1 Aldrich Chemical) is presumed to be a product obtained by oxidative cleavage of tetrahydrophthalic anhydride. The above results clearly demonstrate the beneficial effect of peroxide treatment. However, it should also be noted that, aside from the above results, some of the above and other samples, from the present process, exceed performance specifications for permanent press agents and may be better in performance than other available candidates. With regard to the pilot plant BCTA, the material contained more impurities than is apt to be typical of the pilot plant product. A poor separation was obtained in the filtration of the precursor TMBTC, and better filtration and separation is obtainable.

The laboratory prepared BTCA was prepared on a laboratory scale by a process involving the same steps as described for an exemplary pilot plant process herein, but with variations noted in Table 2; also, an acid neutralization step was not used.

It was found that Pilot Plant BTCA, as separated from aqueous solution by filtration, contained residual $H_2SO_4$. Titration with NaOH solution was utilized to determine the $H_2SO_4$ quantitatively, so it could be neutralized. A sample of commercial BTCA (Aldrich Chemical) as a 12% solution was determined to have a pH of 1.68 at 25° C., 1.76 at 24° C., and 1.85 at 22° C. Titration of a 12 wt % solution of pilot plant wet cake found that the material contained 4.06 wt % sulfuric acid. A 785.6 g sample of pilot plant BTCA was slurried in a flask with 202 g deionized water. The calculated 31.88 g $H_2SO_4$ content would require 26 g NaOH for neutralization. A 51.4 gram quantity of a 50% aqueous solution of NaOH was slowly added to the stirred slurry at 80° C. to provide a stoichiometrically equivalent amount of sodium hydroxide. The slurry was cooled to 35° C. and filtered, affording 436.3 g of BTCA crystals. The pH of a 12% solution of this caustic-treated BTCA crystals was 1.80 at 24° C. The material is referred to as "after neutralization" in Table 2 above, as "Finished BTCA" in Table 3 below, and "Monsanto BTCA" in Table 4 below. A slurry is preferable to a solution for the neutralization in order to avoid high yield losses due to the solubility of the BTCA. In commercial production, it will be desirable to recycle the filtrate to subsequent batch neutralization procedures in order to lower BTCA losses.

EXAMPLE 9

An alternate procedure was utilized to appraise color development of BTCA samples upon heating. In this procedure 10 grams of BTCA was dissolved in 93 grams of ethylene glycol and the solution was refluxed at 198° C. for 24 hours. The absorbance at 400 nm was then measured. Results are reported in Tables 3 and 4. Ethylene glycol was used to provide a base line; it was assigned a Factor of 1.

TABLE 3

HEAT DISCOLORATION TEST
EFFECTS OF THE VARIOUS PROCESSING STEPS

| | | 40 nm Absorbance Factor | |
|---|---|---|---|
| Sample | $H_2O_2$ Treated | Before Heating | After Heating |
| 1. Ethylene Glycol | | | 1.0 |
| 2. Finished BTCA | X | 1.4 | 6.3 |
| 3. w/o neutralization of $H_2SO_4$ | X | 4.2 | 8.1 |
| 4. w/o $H_2O_2$ treatment | | 4.8 | 8.5 |
| 5. w/o water extraction of TMBTC | X | 5.1 | 12.7 |

Table 3 shows the effect of various processing steps. It is apparent that omission of any of the steps results in more color, both before and after the samples are heated.

TABLE 4

HEAT DISCOLORATION TEST
BTCA IN ETHYLENE GLYCOL[1]

| | | 400 nm Absorbance Factor | |
|---|---|---|---|
| Sample | $H_2O_2$ Treated | Before Heating | After Heating |
| 1. Ethylene Glycol | | | 1.0 |
| 2. Aldrich BTCA | | 7.99 | 21.5 |
| 3. Aldrich BTCA | X[2] | 13.2 | 9.7 |
| 4. Commercial BTCA #2 | | 3.7 | 10.0 |
| 5. Monsanto BTCA | | 4.8 | 8.5 |
| 6. Monsanto BTCA | X | 1.4 | 6.3 |

[1]Heated at 198° C. for 24 hours.
[2]Treated in the laboratory following purchase.

In Table 4, Monsanto BTCA prepared by the present process, both with and without peroxide treatment, is compared to commercial samples. The Monsanto BTCA #6, a finished BTCA with peroxide treatment, is superior to the commercial samples, and also shows advantage over a Monsanto sample which had not been peroxide treated. The commercial BTCA #2 is a commercial sample of unknown source. The reference to Aldrich BTCA as peroxide treated refers to a treatment carried out and reported in Table 4, rather than indicating that the material as available has been peroxide treated.

EXAMPLE 10

Figure 4:
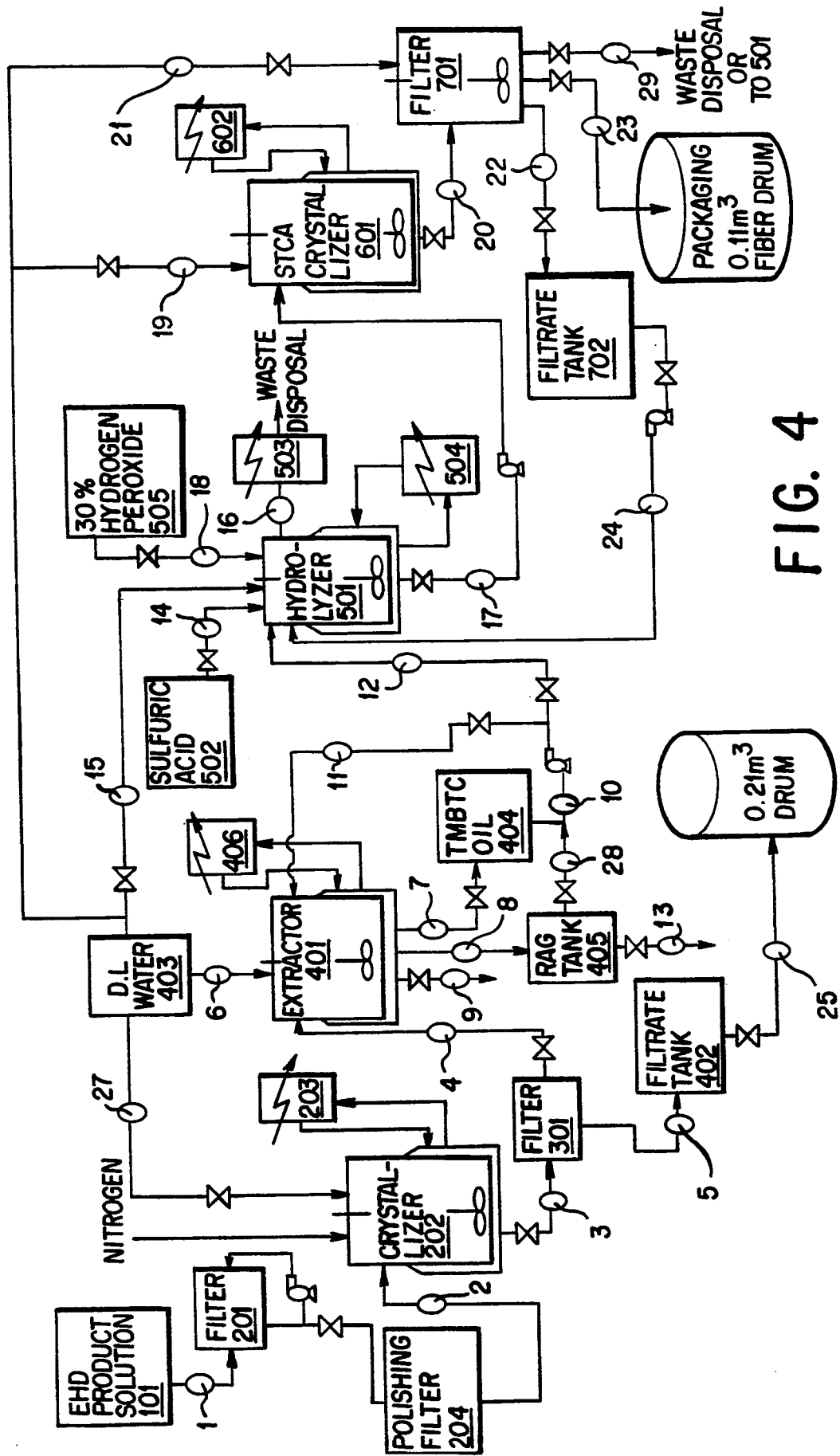
FIG. 4 is a flow sheet of an exemplary process for preparing BTCA.

The drawing, FIG. 4, is a process flow diagram illustrating the various unit processes and flow streams involved in preparing butanetetracarboxylic acid in accord with an exemplary embodiment of the present invention.

The present process is especially useful for preparing butanetetracarboxylic acid from tetramethyl butanetetracarboxylate obtained as product in an electrohydrodimerization, as described in a copending patent application identified above. The tetramethyl butanetetracarboxylate (TMBTC) from an electrohydrodimerization (EHD) will ordinarily be provided as a methanol solution, containing for example 24-25% by weight of TMBTC. To describe the process in accord with the diagram, the solution of TMBTC in feed storage tank 101 is pumped as stream 1 through a filter 201 and a polishing filter 204 and stream 2 to crystallizer 202. The TMBTC solution as provided contains small amounts of black particulates, presumably graphite from electrode erosion in the EHD cells. The particulates can cause formation of a rag layer during an extraction step which is part of the present process and separation of oil and water phases in the extraction is greatly improved by prior removal of particulates. The separation requires much less time in the substantial absence of particulates, so the filtration is clearly advantageous when particulates are present. Of course, the filtrations would not be very useful if particulates were not present, as might be the case if the TMBTC were prepared in a process using metal electrodes, or in a process other than an EHD process. In the filtration the first filter, 201, is used to remove the particulates, for example by employing diatomaceous earth by adding it to feed storage tank 101, which is stirred to maintain a suspension. The intention is to provide sufficient diatomaceous earth to form about a 1.27 cm layer on the filter cloth in filter 201. The filtrate from 201 is pumped back to filter 201 until a clear filtrate is observed, which is then pumped forward to polishing filter 204, which is preferably equivalent to 6 microns or finer filter paper, and then to crystallizer 202.

The filtered solution contains, for example, about 25% by weight TMBTC. The TMBTC is crystallized from the solution by cooling to near −10° C. while stirring. Crystallization will occur at 0° C. or below, but the amount recovered increases markedly as the temperature is lowered from 0° to −10° C. There is still some further improvement below −10° C., but this is offset by the increasing cooling costs and time to achieve the cooling with available refrigeration means. Ordinarily a temperature of about −10° C. will be preferred, but temperatures of −15° C., or −20° C. or lower can be employed. At −10° C. about 88% of the TMBTC crystallizes from solution.

The TMBTC recovery can be increased by adding water to the methanol solution containing TMBTC. The addition of water at about three times the weight of the solution, i.e. to have about 75% water, improves the TMBTC recovery at −10° C. to about 98%, and also partitions more of the solution components into the filtrate. However, 75% water uses a large volume in the crystallizer vessel, and it will probably be expedient to use a lesser amount of water, say 25%, and accept a somewhat lower recovery, say 93% or so.

The crystallizer 202 is maintained under nitrogen as a precaution, in view of the flammability of methanol.

The mixture of crystals and liquor from the crystallizer is sent by stream 3 to filter 301, where the crystals are separated from the liquor. The crystals are then melted by heating to a temperature of about 75° C., or higher, and the melt is forwarded as stream 4 to extractor 401. In the extractor deionized water from tank 403 as stream 6 is mixed with the melt and then separated into water and oil phases in order to remove salt and other water soluble components. The temperature in the extractor is kept at about 70°–76° C. to avoid solids formation. TMBTC melts in a range of about 55°–60° C., but the meso-isomer has a melting point of 76° C. Temperatures sufficient to avoid solids formation are preferable. The extraction will usually employ about equal weight parts TMBTC and water, e.g. to 171 parts TMBTC, 175 parts water is added with heating to 75° C., and agitation is started and continued for about 30 minutes. Agitation is stopped, and phase separation commences. A particulate-free mass separates in minutes at 75° C., but generally some particulates are present and a rag layer will form between a lower oil TMBTC layer and an upper water layer. A typical separation is 17.9 parts of rag layer, 141.9 parts of lower oil layer and 184.6 parts of upper water layer. The lower oil layer is sent by stream 7 to TMBTC oil hold tank 404. The rag layer as stream 8 is stored in a tank 405 where the rag will slowly separate, and the oil may be recovered as stream 28 and returned to the extractor, or it can be slowly isolated and periodically added to hydrolyzer 501, while water is disposed of in stream 13. The water layer in extractor 401 contains about 1% TMBTC, and is collected from stream 9 for disposal. The oil layer from 404 is returned to the extractor by stream 11 and the extraction is repeated, using, for example, 147 parts of deionized water. The TMBTC oil layer from 404, about 136.8 parts, is then sent via streams 10 and 12 to hydrolyzer 501. The hydrolyzer is a jacketed, glass-lined vessel provided with an agitator and condenser, and equipped with ample heating means. The hydrolysis is conducted with an amount of water of only about twice the weight of the TMBTC, and a high concentration of mineral acid catalyst. Also, methanol is distilled from the reaction mixture in order to drive the reaction toward completion. To 136.8 parts of TMBTC, 127 parts of water is added through stream 15 and agitation is started. A charge of 38.1 parts sulfuric acid is added, from two sources, the BTCA crystallizer filtrate tank, 702, and make-up from sulfuric acid bottles, 502. To provide the acid, the hydrolyzer is charged with 203 parts of solution from the tank 702 through stream 24 and 1.1 parts of new sulfuric acid from bottles 502 through stream 14. In addition to sulfuric acid, the filtrate also provides the BTCA heel from the BTCA crystallization and separation, with the use of the heel providing a near stoichiometric recovery of the BCTA. The BCTA filtrate contains 17% by weight BCTA at ambient temperature. The hydrolysis may be completed by about 4.5 hours reaction with simultaneous stripping of methanol, or by refluxing until equilibrium is reached, followed by stripping of methanol. In the latter procedure, about 76% hydrolysis is achieved in 1 hour, and this is followed by distillation of methanol and water for about 3 hours, with addition of water in amount to replace distillate. An appropriate addition rate maintains a pot temperature of 103.5° C. However, at the beginning of the distillation the pot temperature is depressed by the high concentration of methanol, and water is added at 5.57 parts per minute until the temperature reaches 103.5° C. After three hours of distillation, the water addition is stopped and distillation continued untill the pot temperature reaches 111° C. The hydrolyzer distillate at 503 can be disposed of, being water and a small concentration of methanol. The hydrolysis mass in the hydrolyzer 501 will contain some color or color-forming bodies. These can be greatly reduced by a simple oxidation procedure. An oxidizing agent which will oxidize the color and color-forming bodies, and not leave objectionable amounts of color-causing contaminants, is appropriate for use. It has been found that hydrogen peroxide serves very well. The reaction with hydrogen peroxide is performed in the hydrolyzer 501 after the hydrolyzed solution is cooled to a temperature of between 45 and 55° C. To the hydrolyzed solution present in about 308 weight parts, a charge of 2.5 parts of 30% hydrogen peroxide in water is added from container 505 through stream 18. The solution is agitated for about 30 minutes at 45°–55° C. Then the temperature is increased and the solution is refluxed for about 30 minutes or as necessary to decompose excess peroxide and such peracids as are present.

The absence of peroxides and peracids is determined by testing with acidified starch-iodide paper.

A 310.7 parts amount of hydrolyzed and oxidized reaction mass from hydrolyzer 501 is pumped as hot liquid through stream 17 to BTCA crystallizer 601. The crystallizer is a glass-lined tank equipped with cooling and agitation. The liquid is cooled to about 22° C., by tower water, and product allowed to crystallize. When crystallization appears complete, the 310.7 parts of crystallization mass is transferred as stream 20 to filter 701. The aqueous sulfuric acid filtrate is corrosive, and therefore the filter will be of corrosion resistant materials. A suitable filter medium is, for example, 3–6 micron screen or filter paper. The crystallizer mass separates into 105 parts of BTCA crystals and 202 parts of filtrate. The filtrate is sent as stream 22 to tank 702 for recycle as stream 24 back to the hydrolyzer as catalyst and heel. In a crystal washing step, 24.7 parts of deionized water is added by stream 21 to the filter and the BTCA reslurried. The resulting 30 parts of filtrate is preferably directed to filter tank 702, or alternatively as stream 29 for waste disposal or recycle. The BTCA crystals are optionally dried by warm air, or may be packaged for shipment with water analysis being reported, being transferred to drums by line 23. In repeated production runs, it is anticipated that the filtrate from the BTCA will be recycled to the next batch filtration, thereby making the BTCA recovery near quantitative. The filtrate liquor contains approximately 16.5% BTCA. A problem with impurities may develop if corrosion occurs, or as by-products build up in the filtrate. If BTCA quality were affected, the problem could be minimized by removing a portion of the filtrate after each batch. If filtrate quality considerations require disposing of large portions of the filtrate, it will be desirable to use lower than ambient temperature for the BTCA crystallization in order to increase the percentage of BTCA which crystallizes. An alternative is to leave the BTCA in solution and to supply it for use in solution form.

As discussed hereinabove, BTCA produced in the present process may contain substantial amounts of residual acid catalyst. In a procedure (not illustrated in the Flow-Diagram of FIG. 4), the BTCA product can be treated with base to remove the acid by neutralization. It will generally be desirable to provide sufficient base, e.g. NaOH, to completely neutralize the acid. However, partial neutralization is also beneficial, so amounts of base stoichiometrically equivalent to or less than equivalent to the acid can be used. An excess of base can be used, but will tend to form salts within the BTCA, causing loss due to aqueous solubility. In order to minimize BTCA yield losses due to solubility, it will be desirable to use only small amounts of water in the neutralization to form a slurry of the BTCA, into which a caustic solution can be stirred slowly. The BTCA is then filtered from the slurry in crystalline form.

Bases in general can be used for the neutralization, although solubility considerations may make some inconvenient. Alkali metal hydroxides, however, particularly sodium and potassium hydroxides, are convenient and readily available. Other known methods of removing acid contaminants can be used, including those involving ion exchange resins. In view of the relatively high solubility of BTCA in water, it will be desirable to save the filtrate for return to a subsequent neutralization batch, and to employ cooling for the separation, to ambient or possibly lower temperatures. In some applications for BTCA, the use will be in a controlled pH environment, or otherwise involve neutralization of residual acid, so that neutralization is not needed as part of the preparation process.

Table 5 is a Materials Balance table setting forth the projected weight parts of various components in the streams of the Flow Diagram of FIG. 4, when the present process is carried out in accordance with the flow diagram and the foregoing description, and supplying materials as indicated in the table. In the table, DMM stands for dimethyl maleate, DMS for dimethyl succinate, and MeO-DMS for methoxydimethylsuccinate.

TABLE 5

| COMPONENT | MW | 1 | 2 | 3 | 4 | 5 | 6A | 6B | 7 | 8 | 9A |
|---|---|---|---|---|---|---|---|---|---|---|---|
| BTCA | 234.16 | 0.0 | 0.0 | 0.0 | 0.0 | 0.0 | 0.0 | 0.0 | 0.0 | 0.0 | 0.0 |
| TMBTC | 290.27 | 147.8 | 147.8 | 147.8 | 133.5 | 14.3 | 0.0 | 0.0 | 129.8 | 0.2 | 1.7 |
| DMM | 144.13 | 10.2 | 10.2 | 10.2 | 0.0 | 10.2 | 0.0 | 0.0 | 0.0 | 0.0 | 0.0 |
| DMS | 146.14 | 29.2 | 29.2 | 29.2 | 2.4 | 26.7 | 0.0 | 0.0 | 1.5 | 0.0 | 0.8 |
| MeO-DMS | 176.17 | 16.2 | 16.2 | 16.2 | 0.0 | 16.2 | 0.0 | 0.0 | | | |
| MeOH | 32.04 | 367.6 | 367.6 | 367.6 | 34.4 | 333.3 | 0.0 | 0.0 | 5.1 | 8.8 | 20.5 |
| NaOAc | 82.03 | 5.8 | 5.8 | 5.8 | 0.5 | 5.3 | 0.0 | 0.0 | 0.0 | 0.0 | 0.5 |
| Water | 18.01 | | | 72.9 | 0.4 | 72.6 | 175.0 | 147.0 | 5.2 | 8.8 | 161.1 |
| $H_2SO_4$ | 98.08 | | | | | | | 0.0 | | | |
| $H_2O_2$ | 34.01 | | | | | | | 0.0 | | | |
| Graphite | 12.01 | 0.0 | | | | | | 0.0 | | | |
| Maleic Acid | 116.07 | | | | | | | 0.0 | | | |
| Succinic Acid | 118.09 | | | | | | | 0.0 | | | |
| Fumaric Acid | 116.07 | | | | | | | 0.0 | | | |
| 2-MeO-Succinic Acid | 148.11 | | | | | | | 0.0 | | | |
| Totals | | 576.8 | 576.8 | 649.7 | 171.2 | 478.6 | 175.0 | 147.0 | 17.9 | 184.6 | 136.8 |

| COMPONENT | 9B | 10 | 11 | 12 | 13 | 14 | 15 | 16 | 17 | 18 |
|---|---|---|---|---|---|---|---|---|---|---|
| BTCA | 0.0 | 0.0 | 0.0 | 0.0 | 0.0 | 0.0 | 0.0 | 0.0 | 138.3 | 0.0 |
| TMBTC | 1.7 | 130.0 | 130.0 | 130.0 | 0.0 | 0.0 | 0.0 | 0.0 | 0.0 | 0.0 |
| DMM | 0.0 | 0.0 | 0.0 | 0.0 | 0.0 | 0.0 | 0.0 | 0.0 | 0.0 | 0.0 |
| DMS | 0.0 | 1.5 | 1.5 | 1.5 | 0.0 | 0.0 | 0.0 | 0.0 | 0.0 | 0.0 |
| MeO-DMS | 0.0 | | | | 0.0 | 0.0 | 0.0 | 0.0 | 0.0 | 0.0 |
| MeOH | 5.1 | 5.1 | 5.1 | 0.0 | 8.8 | 0.0 | 0.0 | 56.8 | 0.0 | 0.0 |
| NaOAc | 0.0 | 0.0 | 0.0 | 0.0 | 0.0 | 0.0 | 0.0 | 0.0 | 0.0 | 0.0 |
| Water | 147.0 | 5.2 | 5.2 | 5.2 | 8.8 | 0.1 | 1464.0 | 1438.4 | 133.0 | 1.9 |
| $H_2SO_4$ | 0.0 | | | | | 1.1 | | | 38.2 | |

TABLE 5-continued

| | | | | | | | | | | |
|---|---|---|---|---|---|---|---|---|---|---|
| H2O2 | 0.0 | | | | | | | | | 0.8 |
| Graphite | 0.0 | | | | | | | | | |
| Maleic Acid | 0.0 | | | | | | | | | |
| Succinic Acid | 0.0 | | | | | | 1.2 | | | |
| Fumaric Acid | 0.0 | | | | | | | | | |
| 2-MeO-Succinic Acid | 0.0 | | | | | | | | | |
| Totals | 184.6 | 153.8 | 141.9 | 136.8 | 17.6 | 1.2 | 1464.0 | 1495.2 | 310.7 | 2.8 |

| | STREAM | | | | | | | | | |
|---|---|---|---|---|---|---|---|---|---|---|
| COMPONENT | 19 | 20 | 21 | 22 | 23 | 24 | 25 | 27 | 28 | 29 |
| BTCA | 0.0 | 138.3 | 0.0 | 33.4 | 100.0 | 33.4 | 0.0 | 0.0 | 0.0 | 4.9 |
| TMBTC | 0.0 | 0.0 | 0.0 | 0.0 | 0.0 | 0.0 | 14.3 | 0.0 | 2.0 | 0.0 |
| DMM | 0.0 | 0.0 | 0.0 | 0.0 | 0.0 | 0.0 | 10.2 | 0.0 | 0.0 | 0.0 |
| DMS | 0.0 | 0.0 | 0.0 | 0.0 | 0.0 | 0.0 | 26.7 | 0.0 | 0.0 | 0.0 |
| MeO-DMS | 0.0 | 0.0 | 0.0 | 0.0 | 0.0 | 0.0 | 16.2 | 0.0 | 0.0 | 0.0 |
| MeOH | 0.0 | 0.0 | 0.0 | 0.0 | 0.0 | 0.0 | 333.2 | 73.0 | 0.0 | 0.0 |
| NaOAc | 0.0 | 0.0 | 0.0 | 0.0 | 0.0 | 0.0 | 5.3 | 0.0 | 0.0 | 0.0 |
| Water | | 133.0 | 24.7 | 131.8 | | 131.8 | 72.6 | | | 25.7 |
| H2SO4 | | 38.2 | | 37.0 | | 37.0 | | | | 0.0 |
| H2O2 | | | | | | | | | | 0.0 |
| Graphite | | | | | | | | | | 0.0 |
| Maleic Acid | | | | | | | | | | 0.0 |
| Succinic Acid | | 1.2 | | | 1.2 | 0.8 | | | | 0.0 |
| Fumaric Acid | | | | | | | | | | 0.0 |
| 2-MeO-Succinic Acid | | | | | | | | | 0.0 | |
| Totals | 0.0 | 310.7 | 24.7 | 202.2 | 101.2 | 203.0 | 478.5 | 73.0 | 0.3 | 30.6 |

For the hydrolysis step of the process, a strong acid is definitely preferred, i.e. an acid which is highly dissociated in aqueous media. Mineral acids, such as sulfuric acid and phosphoric acid, and organosulfonic acids, such as, benzenesulfonic acid and p-toluenesulfonic acid, can be used. Hydrochloric acid can also be used, but has the disadvantage of volatility, causing volatility losses, and of corrosiveness to equipment. Sulfuric acid works very well and will ordinarily be selected for use because of effectiveness, low cost and availability.

EXAMPLE 11

Tests were conducted to determine the effect of temperature on the degree of recovery of tetramethyl butanetetracarboxylate from methanol, and the solubility of the compound in methanol at temperatures in the range of interest. The starting concentration was about 25% of the TMBTC compound. Results are reported in Table 6.

TABLE 6

| Temp. (°C.) | Recovery (%) | Solubility (%) |
|---|---|---|
| −11 | 87.8 | 5.07 |
| −7 | 83.5 | 6.49 |
| −6 | 82.2 | 7.32 |
| −1 | 78.6 | 9.22 |

A methanol solution containing TMBTC and various impurities was separated by crystallization and filtration into 33% crystals and 67% filtrate, and partition of the various components between crystals and filtrate was determined at −10° C. temperature with results reported in Table 7.

TABLE 7

| | TMBTC (%) | MeOH (%) | DMM (%) | DMS (%) | MeO-DMS (%) |
|---|---|---|---|---|---|
| Crystals | 2.7 | 0 | 7.4 | 0 | 83.2 |
| Filtrate | 97.3 | 100 | 92.6 | 100 | 16.8 |

From the results in Table 6 it is evident that lower temperatures markedly improve TMBTC recovery, with −11° C., the lowest temperature shown, giving the best results. The results in Table 5 show that the crystallization is an effective means to separate TMBTC from various impurities, as well as from the methanol solvent.

EXAMPLE 12

The effect of water on the recovery of TMBTC from methanol solution was tested, employing about a 25% TMBTC concentration and a −10° C. crystallization temperature. Results are reported in Table 8.

TABLE 8

| % Water | % TMBTC Recovered |
|---|---|
| 0 | 88.1 |
| 5 | 89.9 |
| 10 | 90.6 |
| 20 | 92.9 |
| 40 | 94.1 |
| 75 | 97.6 |

The percentages of water are based on the total solution, i.e. 75% water means a solution with 75% water content. It is evident that the recovery is improved by increasing the water content. Of course, additional water utilizes space in the crystallizer, thereby lessening the payload of TMBTC.

The use of water in the crystallization medium can improve the separation from dimethyl succinate, although this will vary considerably with the percentages of water employed. Table 9 shows the variance in TMBTC composition with % water content.

TABLE 9

| | COMPOSITION OF TMBTC | | | |
|---|---|---|---|---|
| Water (%) | TMBTC (%) | DMS (%) | CH3OH (%) | Water (%) |
| 0 | 88.1 | 10.6 | 6.0 | 0.3 |
| 5 | 77.8 | 12.7 | 8.0 | 1.5 |
| 10 | 75.3 | 13.1 | 8.9 | 2.7 |
| 20 | 75.2 | 10.8 | 8.3 | 5.7 |
| 40 | 75.0 | 9.2 | 5.8 | 10.0 |
| 75 | 73.5 | 5.6 | 2.6 | 18.3 |

Filtrations of the TMBTC solution have been found very useful for their effect upon later extraction procedures, particularly when the solutions were obtained by EHD reactions. The filtrations are employed to filter out insoluble impurities from the TMBTC solutions. In a particular case, an unfiltered EHD solution took up about ⅓ of the volume of an extractor with a rag layer, which resisted separation. With a filtered EHD solution, the rag layer was only about 5% of mass.

The starting TMBTC solution utilized herein, as obtained by an EHD reaction of dimethyl maleate, is characterized by the presence of small amounts of particular reactants, by-products and other impurities. Among those materials included are dimethyl maleate, dimethyl succinate, and methoxydimethyl succinate. These materials are separated fairly effectively in a crystallization and filtration step, as the materials largely remain in the methanol and go to filtrate, while the TMBTC is filtered out as crystals.

Water extractions, as used in the processing, are useful for removing electrolyte salt and some color materials. Some methanol is also removed, but this has little significance as methanol is produced and removed downstream in the hydrolysis stage. A TMBTC solution, as provided from an EHD reaction, has a yellow color. This can be from corrosion of connections, e.g. titanium connections, on EHD electrodes, and from organic color bodies. The water extractions mostly remove the color from the titanium, and partially remove that from organic contaminants. A second extraction appears to remove color beyond that removed by the first extraction. However, the number of extractions to be used will depend upon the degree of contamination, as well as the time and efficiency of the extraction procedure. Also the extractions can be tailored to that which is appropriate in conjunction with a later oxidation treatment to have a sufficient removal of color or color-forming materials. The extractions also remove salts, e.g. sodium acetate. The water extractions can very suitably be performed with the tetramethyl butanetetracarboxylate being the material purified, as this ester has very limited water solubility. In contrast, the downstream hydrolysis product, butanetetracarboxylic acid, has a fair degree of water solubility and would not lend itself to efficient extraction. The term "extraction" is used herein in the sense that the TMBTC is washed with water to extract impurities therefrom, while the TMBTC itself is not dissolved in the aqueous system. For the extractions, any effective way of mixing the TMBTC with an aqueous system, following by separation can be used. Rather than the batch system illustrated herein, a counter-current system could be employed in which streams are mixed and then separated.

There are various possible approaches and routes to preparation of butanetetracarboxylic acid which do not involve tetraalkyl butanetetracarboxylates. From theoretical considerations, tetraalkyl butanetetracarboxylates might be expected to be difficult to hydrolyze, as involving four electron-withdrawing groups on adjacent carbon atoms. However, using procedures in accordance with the present invention it has been found feasible to hydrolyze tetraalkyl butanetetracarboxylates to virtually 100% completion, hydrolyzing all four ester groups, in reasonable reaction times and with nearly quantitative yields; and to conduct an overall process with various purification procedures, starting with a tetraalkyl-butanetetracarboxylate still in its preparative reaction mixture, as e.g. an EHD electrolysis solution, and obtain butanetetracarboxylic acid of acceptable purity in overall yield of 80–85%.

What is claimed is:

1. The process of producing 1,2,3,4-butanetetracarboxylic acid containing only low levels of color-causing materials which comprises hydrolyzing tetramethyl 1,2,3,4-butanetetracarboxylate which contains color causing materials present because of the method of preparation, which method comprises subjecting a liquid medium comprising a substantial concentration of dimethyl maleate, a supporting electrolyte salt, and methanol to electrolysis in an electrolysis cell to effect a reductive coupling of the dimethyl maleate to yield tetramethyl 1,2,3,4-butanetetracarboxylate, and thereafter separating the tetramethyl 1,2,3,4-butanetetracarboxylate from the electrolysis medium by cooling and crystallization, the hydrolysis involving treating the tetramethyl 1,2,3,4-butanetetracarboxylate with water and an acid hydrolysis catalyst and heating to a temperature sufficient to hydrolyze the tetramethyl 1,2,3,4-butanetetracarboxylate and distill methanol and distilling methanol as the hydrolysis reaction proceeds, and treating the resulting aqueous mixture containing 1,2,3,4-butanetetracarboxylic acid with aqueous hydrogen peroxide for a time sufficient to remove substantial amounts of the color-causing materials, as characterized by a color development appraisal test.

2. The process of claim 1 in which the hydrogen peroxide-treated aqueous mixture of 1,2,3,4-butanetetracarboxylic acid is maintained at temperatures up to about 55° C. during the process stage for the removal of color-causing materials and thereafter heated to higher temperatures to decompose excess peroxide.

3. The process of claim 1 in which the acid hydrolysis catalyst is sulfuric acid and the hydrolysis of the tetramethyl 1,2,3,4-butanetetracarboxylate is conducted with a mixture having at least 25% by weight of organic material and a gram equivalents sulfuric acid/hydrolysis mixture ratio of at least 1/1 at distillation temperatures with distillation of methanol and water and addition of water to replace that distilled, with substantially complete hydrolysis within about six hours.

4. The process of claim 1 in which the 1,2,3,4-butanetetracarboxylic acid is treated with sodium hydroxide to remove residual acid hydrolysis catalyst.

5. The process of claim 1 in which the color development appraisal test comprises:
   (a) measuring an absorbance for ethylene glycol at 400 nm;
   (b) forming a solution of the 1,2,3,4-butanetetraacarboxylic acid in the ethylene glycol at a concentration of about 10% by weight of the 1,2,3,4-butanetetracarboxylic acid in the ethylene glycol;
   (c) heating the solution from Step (b) at reflux temperatures for a period of 24 hours;
   (d) cooling the solution from Step (c) to ambient temperatures;
   (e) measuring an absorbance for the solution from Step (d) at 400 nm; and
   (f) calculating an absorbance for the solution from Step (e)/absorbance for ethylene glycol from Step (a) ratio to establish an absorbance factor for the solution relative to the absorbance for ethylene glycol.

* * * * *